United States Patent
Sherry et al.

(10) Patent No.: US 11,690,835 B2
(45) Date of Patent: Jul. 4, 2023

(54) FORMULATION

(71) Applicant: AVIDA MEDICAL LIMITED, Guildford (GB)

(72) Inventors: Robert Arthur Sherry, Nottingham (GB); Weng Sam Tang, Nottingham (GB); John Gerard Barfield, Nottingham (GB)

(73) Assignee: AVIDA MEDICAL LIMITED, Guildford (GB)

( * ) Notice: Subject to any disclaimer, the term of this patent is extended or adjusted under 35 U.S.C. 154(b) by 0 days.

(21) Appl. No.: 16/982,883

(22) PCT Filed: Mar. 22, 2019

(86) PCT No.: PCT/GB2019/050823
§ 371 (c)(1),
(2) Date: Sep. 21, 2020

(87) PCT Pub. No.: WO2019/180456
PCT Pub. Date: Sep. 26, 2019

(65) Prior Publication Data
US 2021/0137904 A1    May 13, 2021

(30) Foreign Application Priority Data
Mar. 22, 2018  (GB) .................... 1804621

(51) Int. Cl.
*A61K 31/4439* (2006.01)
*A61K 9/00* (2006.01)
*A61K 47/14* (2017.01)
*A61K 47/44* (2017.01)

(52) U.S. Cl.
CPC ........ *A61K 31/4439* (2013.01); *A61K 9/0053* (2013.01); *A61K 47/14* (2013.01); *A61K 47/44* (2013.01)

(58) Field of Classification Search
CPC .. A61K 31/4439; A61K 9/0053; A61K 47/14; A61K 47/44
See application file for complete search history.

(56) References Cited

U.S. PATENT DOCUMENTS 5,708,017 A * 1/1998 Dave .................. A61P 1/04
514/393
2013/0115294 A1  5/2013 First

FOREIGN PATENT DOCUMENTS

EP  0 273 890 A1  7/1988
JP  2007161694 A  6/2007

OTHER PUBLICATIONS

Labrafac product information, https://www.gattefosse.com/pharmaceuticals-products/labrafac-lipophile-wl-1349, retrieved Apr. 21, 2022, (Year: 2022).*
Campritol 888 ATO product information, https://www.gattefosse.com/pharmaceuticals-products/compritol-888-ato, retrieved Apr. 21, 2022 (Year: 2022).*
Gattefosse excipients booklet, https://www.gattefosse.com/back/files/Gattefosse_brochure_oral%20drug%20delivery%202020.pdf, retrieved Apr. 21, 2022 (Year: 2022).*
PCT International Preliminary Report on Patentability for corresponding Application No. PCT/GB2019/050823 (dated Sep. 22, 2020).
International Search Report and Written Opinion for corresponding Application No. PCT/GB2019/050823 (dated Jan. 7, 2019).
Great Britain Search Report for Application No. GB 1804621.9 (dated Oct. 18, 2018).
Cruz-Sanmartin et al., "Preparation and Characterization of an Oily Suspension of Omeprazole for Administration in Pediatrics," IJPSR 6(10):4216-4225 (2015).

* cited by examiner

*Primary Examiner* — San Ming R Hui
(74) *Attorney, Agent, or Firm* — Troutman Pepper Hamilton Sanders LLP (Rochester)

(57) ABSTRACT

A formulation having excellent gastric protection properties comprises an active pharmaceutical ingredient and a waxy compound, dispersed in a pharmaceutically acceptable oily carrier. The formulation presents a palatable and stable oral dosage form which is particularly suitable for acid-sensitive active pharmaceutical ingredients, and which is also suitable for active pharmaceutical ingredients which are liable to cause stomach irritation.

25 Claims, No Drawings

FORMULATION

This application is a national stage application under 35 U.S.C. § 371 of PCT Application No. PCT/GB2019/050823, filed Mar. 22, 2019, which claims the priority benefit of Great Britain Patent Application No. 1804621.9, filed Mar. 22, 2018.

FIELD OF THE INVENTION

The present invention relates to a pharmaceutical formulation and in particular, to an oral liquid formulation comprising an acid-sensitive drug.

BACKGROUND OF THE INVENTION

Proton pump inhibitors, or PPIs, are highly effective at reducing the production of acid in the stomach and are indicated in the treatment of gastroesophageal reflux disease (GERD), esophagitis, and other disorders associated with excess acid production. Examples of PPIs include benzimidazole compounds such omeprazole, lansoprazole, dexlansoprazole, esomeprazole, pantoprazole, rabeprazole and ilaprazole. They work by blocking the hydrogen-potassium adenosine triphosphatase enzyme system (H+/K+ ATPase, otherwise known as the 'proton pump'), found in the parietal cells in the stomach wall.

Such compounds may be administered orally and are absorbed into the bloodstream from the small intestine. However, they are known to be acid-sensitive and therefore require formulation in order to allow passage through the stomach without degrading.

To address the problem of acid-sensitivity, drugs of this kind are conventionally formulated as solid dosage forms, such as tablets or capsules, comprising a pH-sensitive protective polymer that is intended to prevent the tablet or capsule from dissolving in the acidic environment found in the stomach, and hence to convey the active ingredient to the small intestine without degradation.

However, for various reasons, some individuals find it difficult or impossible to swallow tablets or capsules. This may be the case, for instance, for young children or the elderly, or for certain patients having other medical conditions. Such patients may find oral liquid formulations more acceptable. Oral liquid formats present their own challenges however, due to potential interactions between the active ingredient and the other materials in the formulation. In addition, there remains the problem that an acid-sensitive active ingredient may degrade before being absorbed.

As stated above, the traditional approach to overcome the limitations in tablet and capsule dosage forms is to protect the dose form with a pH solubility sensitive 'gastric protective' polymer designed to prevent the tablet or capsule from dissolving in the acidic environment found in the stomach but which is soluble at the higher pH found in the gut.

Systems are known in which enteric polymer coated beads (typically around 1 mm in diameter) containing omeprazole are dispersed in liquid, usually water, immediately prior to ingestion by the patient. This is inconvenient for the patient since clean water needs to be available and the product must be prepared immediately prior to ingestion to prevent the enteric coat from dissolving in the neutral pH drinking water.

Oral liquids containing omeprazole are also known. Usually, these are produced as short shelf-life, un-licensed medicines. These oral liquids contain significant amounts of an acid neutralising buffering component such as sodium bicarbonate, to provide some protection of the active ingredient during gastric transit by neutralising stomach acid, but these formulations are also known to be unstable on storage and need to be kept cold in a fridge. The product shelf-life is typically no more than four to twelve weeks. The inclusion of significant amounts of, for example, sodium bicarbonate can also lead to the formulations having an unpleasant taste. Additionally, the relatively large amount of sodium ions present may be unsuitable for patients on a low sodium regime.

Other more general liquid protective systems are known, which contain dissolved pH sensitive polymers; however, such pH sensitive polymers are known to react with the omeprazole and are therefore unsuitable.

U.S. Pat. No. 5,840,737 teaches that stable aqueous solution of omeprazole solutions may be produced by incorporating a buffering agent such as a bicarbonate salt. The formulations have to be stored in a fridge and have a limited useable shelf-life, typically of from one to three months.

U.S. Pat. No. 6,489,346 is a continuation of U.S. Pat. No. 5,840,737 and relates to solid dose formulations produced without an enteric coat, providing that the formulation contains a buffering component such as a bicarbonate salt. Oral liquid compositions are not disclosed.

WO 2007/050294 discloses pharmaceutical preparations and methods that contain enteric polymers formulated in liquid dosage forms. The preparations comprise a mixture of a pharmaceutically active substance, a cellulose acetate phthalate, a solvent including polyethylene glycol, and triacetin.

WO 2011/107855 describes an oral liquid suspension sustained release dosage form containing sustained release pellets suspended in a suspending agent, the pellets comprising seal coated inert pellets having a drug layer comprising a pharmaceutically active ingredient with one or more pharmaceutically acceptable excipients, and a coating layer comprising a rate controlling polymer.

EP 0273890 discloses a dosage form for oral administration of a pharmaceutically active substance in which the pharmaceutically active substance is encapsulated or embedded in a pharmaceutically acceptable non-aqueous liquid. The dosage form is intended for pharmaceutically active substances which have an unpleasant taste, or are unstable in aqueous solution, or both. EP 0273890 is not concerned with gastric protection, nor with acid-labile compounds.

There remains a need for a palatable and stable oral liquid dosage form that is capable of inhibiting or preventing the degradation of acid-sensitive active ingredients during transit through the stomach.

DETAILED DESCRIPTION OF THE INVENTION

The present inventors have found that by directly combining an active ingredient with a waxy substance to form a solid mass, comminuting this solid mass into microparticles, and dispersing the microparticles in a liquid base, a formulation having excellent gastric protection in conditions simulating the acidity of gastric fluid is afforded. The formulation presents a palatable and stable oral dosage form which is particularly suitable for acid-sensitive active pharmaceutical ingredients, and which is also suitable for active pharmaceutical ingredients which are liable to cause stomach irritation.

In accordance with a first aspect of the present invention, there is provided a liquid formulation for oral administration comprising an active pharmaceutical ingredient (API), a waxy compound, and a pharmaceutically acceptable oily carrier, characterised in that particles comprising said active pharmaceutical ingredient and said waxy compound are dispersed in said pharmaceutically acceptable oily carrier.

The liquid formulation of the present invention is of particular use in relation to acid-sensitive APIs; i.e., APIs that are unstable at the pH of gastric acid (also referred to as acid-unstable APIs). Such APIs need to be protected during transit through the stomach.

Dispersed particles comprising the active pharmaceutical ingredient and waxy compound may be referred to as microparticles, or drug-loaded microparticles, and are formed by comminuting a solid mass formed from the active pharmaceutical ingredient and the waxy substance to form particles generally of the order of one to several hundred microns, such as 100 μm-1000 μm.

For example, the microparticles may comprise particles of from around 150 μm to around 400 μm. In one embodiment, the microparticles comprise particles of around 250 μm-400 μm. In another embodiment, the microparticles comprise particles of around 180 μm-250 μm. In another embodiment, the microparticles comprise particles of around 150 μm-180 μm.

The formulation of the present invention is thus a dispersion of drug-loaded microparticles in a suspending oily carrier base. The weight ratio of waxy substance to active pharmaceutical ingredient in the microparticles may vary, for example from 1:10-10:1 w/w. In some examples, the weight ratio of waxy substance to active pharmaceutical ingredient may be 6:1, 5:1, 4:1, 3:1, 2:1, 1:1, or 1:2. However, any weight ratio of waxy substance to active substance in the range of from 1:10-10:1 is suitable.

As mentioned above, the invention is of greatest utility in relation to active pharmaceutical ingredients that are acid-sensitive, i.e., active pharmaceutical ingredients that are altered on contact with an acidic environment. While the technology of the present invention was developed to solve a known problem with acid-sensitive PPIs such as the benzimidazoles omeprazole, lansoprazole, dexlansoprazole, esomeprazole, pantoprazole, rabeprazole, ilaprazole and the like, it is suitable for stabilising acid-sensitive compounds generally. Examples of other acid-sensitive compounds include amylase, aureomycin, bacitracin, beta carotene, cephalosporins, Chloromycetin, cimetidine, cisapride, cladribine, clorazepate, deramciclane, didanosine, digitalis glycosides, dihydrostreptomycin, erythromycin, etoposide, famotidine, hormones (in particular estrogens, insulin, adrenalin and heparin), lipase, milameline, novobiocin, pancreatin, penicillin salts, polymyxin, pravastatin, progabide, protease, quinapril, ranitidine, streptomycin, subtilin, and sulphanilamide. Other acid-sensitive APIs will be known to the person skilled in the art.

APIs included in the liquid formulations of in the present invention may be included in the form of their pharmaceutically acceptable salts; for example, where omeprazole is stated to be the API, salts such as the sodium, potassium and magnesium salts of omeprazole may be used in the formulations. A particularly preferred API for use in the present invention is omeprazole, for example in salt form, such as in the form of its sodium salt.

By "waxy compound", or "wax", is meant an organic compound that is a hydrophobic, malleable solid at and near ambient temperatures. Examples include higher alkanes (i.e., hydrocarbon compounds of the formula $C_nH_{2n+2}$, where n is at least 18, more commonly at least 20 or at least 24, and n is typically up to 40, or up to 60) and lipids, including mono-, di- and tri-glycerides and phospholipids. Waxes typically have melting points above about 40° C. Waxy compounds are insoluble in water (by which is meant having a solubility in distilled water of less than about 1 gram per 100 ml, and typically less than 0.5 gram or less than 0.1 gram per 100 ml), but are generally soluble in organic, nonpolar solvents.

The waxy compound for use in the present invention preferably has a melting point in the range of about 40° C. to about 80° C. Waxy compounds with melting ranges lower than about 40° C. are likely to melt or partially melt in body temperature, thereby compromising the intended function of protecting the API. The use of waxy compounds with melting ranges higher than about 80° C. may be detrimental to heat-sensitive APIs such as omeprazole.

A waxy compound may be classified in terms of its HLB (hydrophile-lipophile) balance, which is indicative of the relationship between the hydrophilic and the hydrophobic groups of the compounds. The waxy compound for use in the present invention preferably has an HLB value of less than 5. For example, the waxy compound may have an HLB value of from about 0 to about 4.9, including any individual value within this range.

Preferably the waxy compound is a long-chain mono- or di-glyceride or a mixture of such compounds.

By long-chain mono- or di-glycerides is meant glycerides with one or two fatty acid residues, those fatty acid residues being greater than 12 carbon atoms in length, and preferably greater than 16 carbon atoms in length. Key characteristics of preferred glycerides are the melting point ranges and HLB values mentioned herein.

Examples of long-chain mono- or di-glyceride or mixtures of such compounds which may be suitable for use in the present invention include Gelucire® 43/01, a hard fat consisting of mono-, di- and tri-glyceride esters of fatty acids ($C_8$ to $C_{18}$), the triester fraction being predominant; Compritol® 888 ATO, a glyceryl behenate consisting of mono- di- and tri-esters of behenic acid ($C_{22}$), the diester fraction being predominant; and Geleol™, a glyceryl monostearate consisting of mono- di- and tri-esters of palmitic ($C_{16}$) and stearic ($C_{18}$) acids. Each of these has a melting point range within the range of about 40° C. to about 80° C. referred to above, and each has an HLB value of less than 5. The skilled person will be aware of other waxy compounds and long-chain mono- and di-glycerides and mixtures thereof that fulfil the above melting ranges and HLB values.

Most preferably the long-chain mono- or diglyceride for use in the present invention contains fatty acid residues of length greater than 20 carbon atoms. Most preferably the mono- or diglyceride is glyceryl behenate. In particularly preferred embodiments, the behenate is a combination of mono- and dibehenate as found in glyceryl behenate EP/NF supplied under the tradename Compitrol® 888 ATO, as described above. Compitrol® 888 ATO has a HLB value of 2 and a melting range of 65-77° C.

Other suitable waxy compounds may include plant and animal waxes such as carnauba wax and beeswax, petrolatum waxes such as microcrystalline wax, and long chain aliphatic esters such as cetyl palmitate. Further examples include long-chain (typically $C_{12}$ and above) fatty acids that are solid at ambient temperature, such as palmitic acid and stearic acid, as well as esters of dicarboxylic acids such as fumaric, succinic and sebacic acid (eg dibutyl sebacate, diethyl sebacate and alkyl fumarates and alkyl succinates).

In addition, certain polyethylene glycols (PEGs) that are solid at ambient temperature may also be suitable, e.g., PEG6000 and analogues thereof. While these are generally readily soluble in water, they are included within the term 'waxy compounds' for the purpose of the present invention.

The oily carrier may comprise a triglyceride-based oil. By "triglyceride-based oil" is meant an oil that is liquid at ambient temperatures and which is made up entirely or largely of triglyceride molecules. Ambient temperatures in this context mean temperatures of the surroundings in which the formulation of the invention is likely to be dispensed in normal use; such temperatures will typically be between 5° C. and 40° C., or between 10° C. and 30° C. Examples of oils made up entirely or largely of triglyceride molecules include vegetable oils, as well as analogous synthetic or semi-synthetic materials, such as medium-chain triglycerides. The triglyceride-based oil may be a mixture of such materials.

Vegetable oils that may be used as, or as part of, the triglyceride-based oil include, without limitation, castor oil, coconut oil, corn oil, ground nut oil, olive oil, palm oil, rapeseed oil, soybean oil, *arachis* oil, and sunflower oil.

Other materials that may be used as, or as part of, the triglyceride-based oil are purified or fractionated triglycerides that may be obtained from vegetable oils or other sources. Such triglycerides may be those referred to as medium chain triglycerides or those referred to as long chain triglycerides. By medium-chain triglycerides (MCTs) is meant triglycerides containing fatty acid residues of 6-12 carbon atoms in length. By long-chain triglycerides (LCTs) is meant triglycerides containing acid residues of more than 12 carbon atoms in length, or more than 16 carbon atoms in length.

The triglyceride-based oil may be a vegetable oil that contains predominantly long chain triglycerides, such as sunflower oil (which comprises high proportions of oleic and linoleic triglycerides) or corn oil (which comprises high proportions of linoleic triglycerides). More preferably, however, the triglyceride-based oil comprises predominantly medium-chain triglycerides, for example caprylic/capric triglycerides, available for example under the trade names Miglyol 812™, Crodamol GTCC™, or Kollisolv MCT60/MCT70™. Medium-chain triglycerides are advantageous because they are bland in flavour compared to other fats and are also more polar than long-chain triglycerides and thus certain active ingredients may be more soluble in the carrier if a medium-chain triglyceride is chosen. Medium-chain triglycerides are also easily metabolised by the human body and are therefore generally suitable for oral ingestion.

The aliphatic chains of the triglycerides may be saturated or unsaturated. Preferably the triglycerides contain mostly aliphatic chains that are saturated. In general, the triglyceride-based oil will contain mixtures of triglycerides with fatty acid residues of differing chain lengths and/or levels of unsaturation. The triglyceride-based oil may also contain minor proportions of mono- and/or di-glycerides, as well as minor amounts of other components such as free fatty acids and other impurities. Minor proportions of mono- and di-glycerides are naturally occurring in vegetable oils, making up approximately 1-6% of the vegetable oil, but are likely to be removed during the refining process. Thus, in this particular context, minor proportions of mono- and di-glycerides typically refers to proportions of between 0 and 6%. Oils of natural origin may be particularly heterogeneous; synthetic or semi-synthetic materials may be more uniform in their composition.

Preferably, the oily carrier comprises only one or more triglyceride oils as described above; that is, it does not contain other carrier substances. However, in an embodiment of the present invention, the carrier may comprise a major proportion of a triglyceride-based oil, and a minor proportion of a waxy compound. Where the carrier comprises a waxy compound and a triglyceride-based oil, the triglyceride-based oil forms the majority of the carrier, ie at least 50% of the carrier by weight. More preferably the triglyceride-based oil constitutes at least 60%, at least 70%, at least 80%, at least 90%, or at least 95% of the carrier by weight. Most preferably the triglyceride-based oil constitutes at least 97% of the carrier. The triglyceride-based oil will normally account for less than 99% by weight of the carrier. Thus, the triglyceride-based oil may account for about 98% by weight of the carrier. Accordingly, the waxy compound makes up a minor proportion of the oily carrier, i.e., it accounts for less than 50% of the carrier by weight. More preferably the waxy compound comprises less than 40%, less than 30%, less than 20%, less than 10%, or less than 5% by weight of the carrier. Most preferably the waxy compound comprises less than 3% of the carrier by weight. In particularly preferred embodiments, the waxy compound comprises approximately 2% w/w of the carrier. The waxy compound and the triglyceride-based oil are as described herein.

The invention is suitable for stabilising acid-sensitive compounds generally but is particularly suitable for stabilising benzimidazole compounds (proton pump inhibitors) that are known to be unstable in the acidic conditions found in the stomach. Examples of such active ingredients are omeprazole, lansoprazole, dexlansoprazole, esomeprazole, pantoprazole, rabeprazole and ilaprazole. The active ingredient will most usually be a single drug compound but may be a mixture of two or more drug compounds.

The concentration of the active pharmaceutical ingredient will depend on the required dose and the amount of the substance that can be put into solution or suspension in the formulation. Where the active pharmaceutical ingredient is a proton pump inhibitor, the proton pump inhibitor may be present at a concentration in the range of from about 1 mg/ml to about 10 mg/ml, for instance about 2 mg/ml, about 4 mg/ml or about 8 mg/ml. For a dose of 5 ml, those concentrations correspond to a unit dose of 10 mg, 20 mg or 40 mg, with the range of about 1 mg/ml to about 10 mg/ml corresponding to 5-50 mg unit doses.

The formulation according to the invention is also beneficial in that it has an acceptable shelf life. By that is meant that, when kept under normal storage conditions, a packaged formulation according to the invention is stable for at least three months, and more preferably for at least six months or for at least twelve months. In this context, "stable" means that at least 90%, and more preferably at least 95% or at least 98% by weight of the active ingredient remains in an active form in the formulation over the stated time period. Studies have demonstrated the chemical compatibility of an API, wax and oil in accordance with the present invention, indicating acceptable shelf life.

The formulation may be put up in unit dose form. For instance, the formulation may be packaged in a sachet containing, for example, a unit dose of any individual value of from 1 ml to 20 ml of the formulation. In currently preferred embodiments of the invention, the dose is 5 ml. Alternatively, the formulation of the invention may be put up in a bulk form from which individual doses may be dispensed as required. The formulation may, for instance, be packaged in a bottle or the like, from which individual doses may be dispensed by pouring into a spoon or other measuring vessel, of from which doses may be dispensed by a metering mechanism, such as a metering pump, or a dosing device, such as a syringe.

The formulation is intended to protect an acid-sensitive drug from the harsh acidity of the stomach but conversely it is also contemplated that the technology could be suitable to protect the stomach from adverse effects caused by a drug, for example in the case of a drug that causes irritation to the stomach lining. Examples of such drugs include ibuprofen and other 2-arylpropionic acids or profens, diclofenac, cyclooxygenase-2 (COX-2) inhibitors (eg celecoxib, etoricoxib, firocoxib, lumiracoxib, parecoxib, rofecoxib and valdecoxib), nitrofurantoin, alendronate, corticosteroids and sulpasalazine. Thus, the present invention also provides a liquid formulation for oral administration comprising an active pharmaceutical ingredient (API), a waxy compound, and a pharmaceutically acceptable oily carrier, characterised in that the API is a substance which is liable to cause stomach irritation, and particles comprising said active pharmaceutical ingredient and said waxy compound are dispersed in said pharmaceutically acceptable oily carrier.

Consequently, the invention further provides a method of treating a patient having or susceptible to a condition that may be ameliorated or prevented by an active pharmaceutical ingredient that is sensitive to the acidity of the patient's stomach and/or that may induce an adverse effect upon the patient's stomach, which method involves oral administration to the patient of an appropriate formulation in accordance with the present invention.

The present invention also provides an oral liquid formulation for use in treating a condition which may be ameliorated or prevented by an active pharmaceutical ingredient that is sensitive to the acidity of a patient's stomach, the formulation comprising an active pharmaceutical ingredient selected from an acid-sensitive active pharmaceutical ingredient, a waxy compound, and a pharmaceutically acceptable oily carrier, particles comprising said active pharmaceutical ingredient and said waxy compound being dispersed in said pharmaceutically acceptable oily carrier; and an oral liquid formulation for use in treating a condition which may be ameliorated or prevented by an active pharmaceutical ingredient that may induce an adverse event upon a patient's stomach, the formulation comprising an active pharmaceutical ingredient selected from an active pharmaceutical ingredient that may induce an adverse event upon a patient's stomach, a waxy compound, and a pharmaceutically acceptable oily carrier, particles comprising said active pharmaceutical ingredient and said waxy compound being dispersed in said pharmaceutically acceptable oily carrier.

The formulations of the present invention may comprise further additional pharmaceutically acceptable components. The additional components may be any appropriate pharmaceutical excipients that are conventionally included in oral liquids, for example flavourants to mask or improve the flavour of the active ingredient and/or the oily carrier, dispersants to keep the active ingredient in suspension, stabilisers and buffers. In particular, the formulation may comprise a pH modifier or stabiliser, for example, meglumine (1-deoxy-1-(methylamino)-D-glucitol), calcium carbonate, sodium carbonate or magnesium carbonate.

Where the formulation comprises a pH modifier, the pH modifier may be present in the range 0.001% to 1% w/v, more preferably in the range 0.005% to 0.5% w/v.

Optionally, at least one anti-oxidant may be included. Examples of anti-oxidants include, without limitation, butylhydroxytoluene (BHT), butylhydroxyanisole (BHA), tert-butylhydroquinone (TBHQ), gallic acid esters such as propyl gallate, tocopherols such as vitamin E acetate, ascorbic acid esters such as ascorbyl palmitate and ascorbyl acetate, carnitine, and/or mixtures thereof.

The formulation of the present invention may also comprise a gel-forming agent such as sodium carboxymethyl cellulose in the microparticles. The gel forming agent will have the effect of forming a gel barrier at the surface of the drug loaded micro particles, restricting diffusion of the drug when the formulation comes into contact with water, such as the aqueous environment encountered during ingestion of the formulation.

The gelling component may be present in the microparticles in amounts typically within the range of from 0.25 to 2% w/w.

In one method, the formulation of the present invention may be prepared by preparing the microparticles and mixing the prepared microparticles with the oily carrier to form a dispersion of the microparticles in the carrier.

Thus, according to a further aspect of the invention, there is provided a process for the preparation of a formulation as described above, which process comprises the steps of
a) combining an active pharmaceutical ingredient with a waxy substance to form a solid mass;
b) comminuting said solid mass into particles; and
c) dispersing said particles in a pharmaceutically acceptable oily carrier.

The active pharmaceutical ingredient for use in the process of the present invention may be provided in the form of a powder. The powder may be sieved in order to remove all lumps and clumps, for example using a 100 mesh sieve. The waxy compound is heated in a suitable vessel, to its melting point range until it melts into a liquid. The sieved API powder may then be incorporated by any suitable means into the molten waxy compound and mixed until homogeneous, with reheating if necessary in order to keep the waxy compound in fluid form and to maximise mixing of the ingredients. The homogenous slurry may then be transferred to a suitable surface and left to cool, for example to room temperature. The resultant solidified waxy mixture may then be triturated into small granulates or particles by any suitable means. For example, a pestle and mortar may be used. Microparticles may then be obtained by sieving the small granulates or particles through a series of sieves, for example, 40/60 mesh, 60/80 mesh and 80/100 mesh.

As an alternative to the melt process described above, microparticles may be produced using a dry-compression process such as that possible in a roller-compaction process or by using a high shear mixer granulator; other suitable means will be known to the person skilled in the art.

In further alternative methods, microparticles may be produced by direct solidification processes. For example, a sieved API powder may be mixed with a molten waxy substance until homogeneous, with gentle reheating if necessary in order to keep the waxy compound in fluid form. The molten mixture may then be added to a portion of a volume of a pharmaceutically acceptable oily carrier and mixed, for example with a high shear mixer. Alternative means of direct solidification of the molten mixture may include other 'top-down' particle size reduction techniques such as high shear mixing or 'bottom-up' particle engineering techniques including prilling, spray-drying and spray-congealing methods, and other methods which will be known to the person skilled in the art. Such methods may be of particular benefit in preparation of the formulations on an industrial scale.

The final formulation may be produced by adding the pharmaceutically active carrier to the microparticles.

For the preparation of commercial-scale amounts of product by any of the methods disclosed herein, an upper size limit, and/or a lower size limit for the microparticles may be set through the selection of an appropriately-sized screen, such that no larger particles are contained in the final product.

Where the pharmaceutically active oily carrier comprises only one or more triglyceride oils, the microparticles and carrier may be mixed to disperse the microparticles in the carrier. Where the carrier also comprises a waxy compound, the waxy compound may be dispensed into a suitable vessel to which is added the triglyceride oil. The mixture may then be heated so as to dissolve or melt the waxy compound and the resultant oil may be left to cool, for example to room temperature, before mixing the microparticles and carrier in order to provide the dispersion.

The invention will now be described in greater detail, by way of illustration only, with reference to the following Examples.

HLB Study

This Example demonstrates the effect of HLB value on the ability of a waxy compound to protect an acid-sensitive API from water ingress or API dissolution when exposed to an acidic medium.

Sample Preparation:

Using a 100 mesh sieve, Omeprazole Sodium powder was sieved to remove all lumps and clumps. Prior to further use, the powder was protected from light and set aside. Waxes for testing were selected in accordance with Table 1 below:

TABLE 1

| HLB value | Material | Melting range |
|---|---|---|
| 1 | Gelucire 43/01 (Hard Fat): | 42-46° C. |
| 2 | Compritol 888 ATO (Glyceryl behenate) | 65-77° C. |
| 3 | Geleol (Glycerol Monostearate 40-55) | 54-64° C. |
| 4 | Monosteol (Propylene glycol monopalmitostearate) | 33-40° C. |
| 5 | Compritol HD5 ATO (Behenoyl polyoxyl-8 glycerides) | 60-67° C. |

In each case, 9.0 g of wax was placed into a suitable vessel and heated on a steam bath until the melting temperature range was reached and the wax had melted into a liquid. While maintaining the temperature, 1.0 g of the previously sieved Omeprazole Sodium powder was incorporated into the molten 'matrix material' and mixed thoroughly to produce a homogenous mixture containing Omeprazole Sodium 10% w/w.

The vessel was swiftly removed from the heat and its contents allowed to cool and solidify in a suitable mould, producing API/Wax matrices as identical circular discs.

pH Challenge:

The matrix discs were individually exposed to 0.1 M HCl. In a first test, an API/Wax matrix disc was placed into 50 ml of 0.1 M HCl, with a magnetic stirrer having a stirring speed set at 2, for a duration of 60 minutes. In a second test, an API/Wax matrix disc was suspended by a suitable fixture, such that it was fully submerged, in 50 ml of 0.1 M HCl, with stirring speed set at 2, for a duration of 60 minutes.

Visual inspection of the extent of discolouration in the media as well as the sample discs is indicative of the extent of acid degradation, allowing an evaluation of the given matrix material. The results are presented in Table 2 below:

TABLE 2

| | | Discolouration | |
|---|---|---|---|
| HLB value | Material tested | Sample disc (free-float/ fixed submerged) | Medium (free-float/ fixed submerged) |
| 1 | Gelucire 43/01 (Hard Fat): | 0/+ | +/+ |
| 2 | Compritol 888 ATO (Glyceryl behenate) | +/++ | ++/++ |
| 3 | Geleol (Glycerol Monostearate 40-55) | ++/+++ | +++/++ |
| 4 | Monosteol (Propylene glycol monopalmitostearate) | +/+ | ++/+ |
| 5 | Compritol HD5 ATO (Behenoyl polyoxyl-8 glycerides) | +++++/++++++ | ++++/+++ |

Key: level of discolouration, visually assessed: 0 = none; + = negligible; ++ = mild; +++ = moderate; ++++ = significant; +++++ = very significant; ++++++ = severe.

In both tests, severe discolouration was observed in API/Wax matrix discs with Compritol HD5 ATO used as the embedding material, showing that this particular material was incapable of protecting the API from acid. The results above indicate that waxes with HLB value of less than 5 may be suitable for use in the present invention.

Example 1

Composition

| Omeprazole: | 20 mg/5 ml |
|---|---|
| Glyceryl dibehenate: | 2.4% w/v |
| Medium Chain Triglycerides (Crodamol ™GTCC): | to 100% |

Process

The omeprazole is present as the sodium salt and corrected to 20 mg/5 ml of omeprazole. Glyceryl dibehenate (2.5 g) was heated with stirring to just above its melting point to form a molten mass. Omeprazole Sodium powder (2.5 g) was added directly to the melt with stirring to form a uniform dispersion. The molten mass was cooled to form a solid dispersion. The cooled mass was milled to form milled micro-particulates with a particle size of around 250 μm. The milled micro-particulates (0.425 g) were added to a liquid base comprising medium chain triglycerides and glyceryl dibehenate (2% w/v) to give 50 ml of the above composition.

The composition of the present Example was tested for gastric resistance.

Dissolution Testing

Dissolution testing was carried out with reference to the British Pharmacopoeia monographs for Omeprazole Gastro-Resistant Tablets/Capsules, but in order to give a higher challenge a pH of 1.2 was applied instead of the pH 4.5 standard.

Samples were drawn from the dissolution medium at designated time points and processed by HPLC for assay levels as soon as possible after drawing of said sample.

The compositions were tested in USP2 dissolution apparatus, 100 rpm paddle speed in pH1.2 Simulated Gastric juice (without enzymes) media. Samples were taken for assay and measurement of degradation product levels at 15, 30 and 45 minutes. The results of the assay and measurement tests are shown in Tables 3, 4 and 5 below.

TABLE 3

Assay of drawn samples: concentration of omeprazole in mg/5 ml

| | Timepoint (minutes) | | |
|---|---|---|---|
| | 15 | 30 | 45 |
| Sample 1 | 0.08 | 0.1 | 0.11 |
| Sample 2 | 0.09 | 0.11 | 0.13 |
| Sample 3 | 0.12 | 0.14 | 0.17 |

TABLE 4

Assay of drawn samples: concentration of omeprazole as a percentage of 20 mg/5 ml

| | Timepoint (minutes) | | |
|---|---|---|---|
| | 15 | 30 | 45 |
| Sample 1 | 0.40 | 0.5 | 0.55 |
| Sample 2 | 0.45 | 0.55 | 0.65 |
| Sample 3 | 0.60 | 0.70 | 0.85 |

TABLE 5

Breakdown of released contents (API & degs); % relative to nominal concentration

| | Time point (minutes) | | | | | | | | |
|---|---|---|---|---|---|---|---|---|---|
| | 15 | | | 30 | | | 45 | | |
| | API | Degs | Total | API | Degs | Total | API | Degs | Total |
| Sample 1 | 0.40 | 1.07 | 1.47 | 0.5 | 2.55 | 3.05 | 0.55 | 3.79 | 4.34 |
| Sample 2 | 0.45 | 1.48 | 1.93 | 0.55 | 2.66 | 3.21 | 0.65 | 3.33 | 3.98 |
| Sample 3 | 0.60 | 4.01 | 4.61 | 0.70 | 6.22 | 6.92 | 0.85 | 7.30 | 8.15 |

The maximum acceptable quantity of API released from the tablet/capsule in 45 min within the acidic medium is 10% of the stated amount.

Suitable gel forming agents such as sodium carboxymethyl cellulose may also be included in this formulation, such that a gel layer is formed on contact with water.

A further variation of the above Example employs a melt extrusion process, in where the drug loaded mass is produced within the extruder and cooled on discharge onto a cooled stainless steel belt.

Example 2

Composition

| | |
|---|---|
| Omeprazole: | 40 mg/5 ml |
| Glyceryl dibehenate: | 2.7% w/v |
| Medium Chain Triglycerides (Crodamol ™GTCC): | to 100% |

Process

Omeprazole Sodium powder was sieved through a 100 mesh sieve to remove all lumps and clumps. Glyceryl dibehenate (2.0 g) was heated in a glass beaker until melted (65-77° C.). The sieved omeprazole sodium powder (1.0 g) was mixed with the molten glyceryl dibehenate until homogenous, with gentle reheating as necessary to keep the glyceryl dibehenate in fluid form. The molten mixture was poured into MCT (40 ml) and mixed using a Silverson mixer at 2500 rpm, to produce solidified microparticles. 25% v/v of 4% w/v glyceryl dibehehate in MCT was added to the mixture and made up to 117.5 ml with MCT to produce a final 1% w/v glyceryl dibehenate in MCT vehicle.

A 5 ml sample of the formulation was exposed to 50 ml of 0.1 M HCl at room temperature, while being gently stirred by a magnetic stirrer. No significant discolouration was observed after 45 min, demonstrating that there is minimal degradation of Omeprazole within the dissolution medium following 45 min of exposure to the acid.

Example 3

Microparticles were prepared following the process of Example 2, and dispersed in a liquid base comprising only Medium Chain Triglycerides; i.e., no glyceryl dibehenate was present in the vehicle.

A 5 ml sample of the formulation was exposed to 50 ml of 0.1 M HCl at room temperature, while being gently stirred by a magnetic stirrer. No significant discolouration was observed after 45 min, demonstrating that there is minimal degradation of Omeprazole within the dissolution medium following 45 min of exposure to the acid.

Example 4

Composition

| | |
|---|---|
| Omeprazole: | 20 mg/5 ml |
| Glyceryl dibehenate: | 2.4% w/v |
| Medium Chain Triglycerides (Crodamol ™GTCC): | to 100% |

Process and Testing

The composition was prepared and tested in accordance with Example 1 above, but samples were taken for assay and measurement of degradation products at 15, 30, 45, and 60-minute time points. The results are presented in Tables 6 and 7 below:

TABLE 6

Gross omeprazole release (API plus degradants): % relative to nominal concentration

| | Time point (minutes) | | | |
|---|---|---|---|---|
| | 15 | 30 | 45 | 60 |
| Sample 1 | 2.61 | 4.23 | 4.23 | 4.76 |
| Sample 2 | 2.43 | 3.28 | 3.58 | 3.94 |
| Sample 3 | 2.58 | 3.36 | 3.78 | 4.73 |
| Sample 4 | 2.63 | 3.71 | 4.22 | 4.68 |

TABLE 7

Breakdown of release of omeprazole and degradants

| | \multicolumn{12}{c}{Time point (minutes)} | | | | | | | | | | | |
|---|---|---|---|---|---|---|---|---|---|---|---|---|
| | 15 | | | 30 | | | 45 | | | 60 | | |
| | API | Degs | Total | API | Degs | Total | API | Degs | Total | API | Degs | Total |
| 1 | 0.25 | 2.36 | 2.61 | 0.17 | 4.06 | 4.23 | 0.11 | 4.12 | 4.23 | 0.07 | 4.69 | 4.76 |
| 2 | 0.20 | 2.23 | 2.43 | 0.15 | 3.13 | 3.28 | 0.09 | 3.49 | 3.58 | 0.04 | 3.90 | 3.94 |
| 3 | 0.19 | 2.39 | 2.58 | 0.12 | 3.24 | 3.36 | 0.07 | 3.71 | 3.78 | 0.03 | 4.70 | 4.73 |
| 4 | 0.26 | 2.37 | 2.63 | 0.19 | 3.52 | 3.71 | 0.09 | 4.13 | 4.22 | 0.04 | 4.64 | 4.68 |

This Example shows that less than 5% of drug contents have been lost into the acidic medium after 60 min of exposure, indicating that the formulation offers excellent gastric protection to the acid-sensitive Omeprazole.

Example 5

Composition

| | |
|---|---|
| Omeprazole: | 20 mg/5 ml |
| Glyceryl dibehenate: | 2.4% w/v |
| Medium Chain Triglycerides (Crodamol ™GTCC): | to 100% |

Process and Testing

The composition was prepared and tested in accordance with Example 1 above, but tested in pH 6.8 dissolution medium instead of in Simulated Gastric Fluid. Samples were taken for assay and measurement of degradation products at 15, 30, 45, 60, 120 and 180-minute time points. The results are presented in Tables 8, 9 and 10 below:

TABLE 8

Gross Omeprazole released (% relative to nominal concentration)

| | \multicolumn{6}{c}{Time point (min)} | | | | | |
|---|---|---|---|---|---|---|
| | 15 | 30 | 45 | 60 | 120 | 180 |
| Sample 1 | 6.91 | 10.22 | 12.91 | 15.44 | 22.92 | 31.36 |
| Sample 2 | 12.84 | 18.64 | 21.80 | 24.18 | 30.50 | 34.82 |
| Sample 3 | 19.64 | 27.11 | 30.25 | 32.63 | 35.54 | 39.58 |
| Sample 4 | 10.36 | 15.90 | 20.40 | 24.38 | 33.23 | 39.50 |
| Sample 5 | 9.64 | 15.02 | 18.38 | 21.34 | 27.97 | 34.84 |
| Sample 6 | 10.39 | 16.67 | 19.95 | 24.18 | 33.52 | 40.72 |

TABLE 9

Breakdown of released contents (API & degs) (% relative to nominal concentration)

| | \multicolumn{9}{c}{Time point (minutes)} | | | | | | | | |
|---|---|---|---|---|---|---|---|---|---|
| | 15 | | | 30 | | | 45 | | |
| | API | Degs | Total | API | Degs | Total | API | Degs | Total |
| Sample 1 | 6.06 | 0.85 | 6.91 | 8.99 | 1.23 | 10.22 | 11.17 | 1.74 | 12.91 |
| Sample 2 | 12.00 | 0.84 | 12.84 | 16.77 | 1.87 | 18.64 | 18.94 | 2.86 | 21.80 |
| Sample 3 | 18.47 | 1.17 | 19.64 | 25.05 | 2.06 | 27.11 | 26.54 | 3.71 | 30.25 |
| Sample 4 | 9.45 | 0.91 | 10.36 | 14.10 | 1.80 | 15.90 | 17.90 | 2.50 | 20.40 |
| Sample 5 | 8.90 | 0.74 | 9.64 | 13.21 | 1.81 | 15.02 | 15.72 | 2.66 | 18.38 |
| Sample 6 | 9.29 | 1.10 | 10.39 | 14.20 | 2.47 | 16.67 | 17.30 | 2.65 | 19.95 |

TABLE 10

Breakdown of released contents (API & degs) (% relative to nominal concentration)

| | \multicolumn{9}{c}{Time point (minutes)} | | | | | | | | |
|---|---|---|---|---|---|---|---|---|---|
| | 60 | | | 120 | | | 180 | | |
| | API | Degs | Total | API | Degs | Total | API | Degs | Total |
| Sample 1 | 13.06 | 2.38 | 15.44 | 18.35 | 4.57 | 22.92 | 24.90 | 6.46 | 31.36 |
| Sample 2 | 20.19 | 3.99 | 24.18 | 23.54 | 6.96 | 30.50 | 27.19 | 7.63 | 34.82 |
| Sample 3 | 27.44 | 5.19 | 32.63 | 28.33 | 7.21 | 35.54 | 30.59 | 8.99 | 39.58 |
| Sample 4 | 20.64 | 3.74 | 24.38 | 27.10 | 6.13 | 33.23 | 30.65 | 8.85 | 39.50 |
| Sample 5 | 18.04 | 3.30 | 21.34 | 22.76 | 5.21 | 27.97 | 27.01 | 7.83 | 34.84 |
| Sample 6 | 20.17 | 4.01 | 24.18 | 27.51 | 6.01 | 33.52 | 31.30 | 9.42 | 40.72 |

The above results demonstrate that the formulation releases the API contents more readily when exposed to the pH 6.8 medium as compared with simulated gastric juice.

Example 7

5.0 g of Glyceryl dibehenate was heated to approximately 76° C. until fully melted into a liquid. While maintaining heat, 5.0 g of previously sieved Omeprazole Sodium powder was added and mixed into the molten Glyceryl dibehenate (Time 0). The temperature of the bulk mixture was maintained at approximately 76° C. with continuous manual stirring, for a total duration of 30 minutes. At Time 5 min, Time 15 min and Time 30 min, a sample (approximately 1 gram) of the slurry was removed from the bulk mixture and allowed to cool on a clean stainless steel surface. The solidified mass was then analysed for drug load, content uniformity and contents of degradation products generated by additional heating. Heating the Omeprazole/Glyceryl Dibehenate mixture for longer period (up to 30 minutes) did not lead to significant increase in the number and levels of degradation products, as illustrated in Table 11 below.

TABLE 11

| | | Degradants (% relative of nominal concentration of Omeprazole) | | | |
|---|---|---|---|---|---|
| | Assay | RRT 1.14 | RRT 1.17 | RRT 1.19 | Total |
| Sample heated for 5 min | 407.71 mg/g | 0.71 | 0.39 | 1.01 | 2.11 |
| Sample heated for 15 min | 409.86 mg/g | 0.69 | 0.39 | 1.02 | 2.10 |
| Sample heated for 30 min | 411.14 mg/g | 0.65 | 0.38 | 1.02 | 2.05 |

The above results indicate that the hot melt process at approximately 76° C. for a prolonged period led to no increase in the formation of Omeprazole degradation products. This is indicative of the suitability of the process for industrial application.

Stability Study

The chemical compatibility of key components of formulations of the present invention was tested over a twelve-month period and the results are presented in Table 12 below.

Composition:

| | |
|---|---|
| Omeprazole (as Omeprazole Sodium) | 0.4% w/v (20 mg/5 mL) |
| Glyceryl Dibehenate | 2% w/v |
| Meglumine (Formula B only) | 0.1% w/v |
| Medium Chain Triglycerides | to 100% v/v |

TABLE 12

| | | Assay (mg/5 mL) | | | | | | | |
|---|---|---|---|---|---|---|---|---|---|
| | Storage condition | Initial | 1 month‡ | 2 months‡ | 3 months | 5 months | 6 months | 9 months | 12 months |
| Formula A | Fridge | 20.7 | N/A | N/A | 19.8 | 19.9 | 20.3 | 20.0 | 20.6 |
| | 25° C./60% RH | | N/A | N/A | 19.9 | 19.8 | 20.6 | 19.3 | 20.6 |
| Formula B | Fridge | 20.9 | N/A | N/A | 20.0 | 19.9 | 20.5 | 19.7 | 20.8 |
| | 25° C./60% RH | | N/A | N/A | 19.6 | 20.0 | 20.2 | 19.8 | 20.6 |

‡Analytical results of 1- and 2-month time points were invalidated due to uncharacteristic chromatograms (Omeprazole Assay acceptance criteria: 19.0 to 21.0 mg/5 mL (i.e. 95.0 to 105.0% of nominal).)

The above results (corrected according to API potency determined immediately following production) show that assay levels remain within specification following 12 months' storage, demonstrating good compatibility of the API with the selected excipients.

The invention claimed is:

1. A liquid formulation for oral administration comprising an active pharmaceutical ingredient, a waxy compound, and a pharmaceutically acceptable oily carrier, characterised in that the active pharmaceutical ingredient is an acid-sensitive active pharmaceutical ingredient, and that in said formulation, particles comprising both said active pharmaceutical ingredient and said waxy compound are dispersed in said pharmaceutically acceptable oily carrier.

2. A liquid formulation as claimed in claim 1, wherein the active pharmaceutical ingredient is a proton pump inhibiting compound.

3. A liquid formulation as claimed in claim 2, wherein the active pharmaceutical ingredient is selected from omeprazole, lansoprazole, dexlansoprazole, esomeprazole, pantoprazole, rabeprazole and ilaprazole.

4. A liquid formulation as claimed in claim 3, wherein the active pharmaceutical ingredient is omeprazole.

5. A liquid formulation as claimed in claim 1, wherein the concentration of the active pharmaceutical ingredient is from 1 mg/ml to 10 mg/ml of the formulation.

6. A liquid formulation as claimed in claim 1 provided as a 5 ml unit dose containing from 5 to 50 mg of the active pharmaceutical ingredient.

7. A liquid formulation as claimed in claim 1, wherein the waxy compound has a melting point range of from 40° C. to 80° C.

8. A liquid formulation as claimed in claim 1, wherein the waxy compound has an HLB value of less than 5.

9. A liquid formulation as claimed in claim 1, wherein the waxy compound is selected from a higher alkane; a lipid; a plant or animal wax; petrolatum wax; a long-chain aliphatic ester; a fatty acid that is solid at ambient temperature; an ester of dicarboxylic acid; and a polyethylene glycol that is solid at ambient temperature.

10. A liquid formulation as claimed in claim 9, wherein the waxy compound is a long-chain mono- or di-glyceride or a mixture of such compounds.

11. A liquid formulation as claimed in claim 10, wherein the waxy compound is a long-chain mono- or diglyceride containing fatty acid residues of length greater than 20 carbon atoms.

12. A liquid formulation as claimed in claim 9, wherein the waxy compound is glyceryl behenate.

13. A liquid formulation as claimed in claim 12, wherein the glyceryl behenate is a mixture of glyceryl monobehenate and glyceryl dibehenate.

14. A liquid formulation as claimed in claim 1, wherein the pharmaceutically acceptable oily carrier comprises a triglyceride-based oil.

15. A liquid formulation as claimed in claim 14, wherein the triglyceride-based oil is a vegetable oil or an analogous synthetic or semi-synthetic material, a mixture of such materials.

16. A liquid formulation as claimed in claim 15, where in the vegetable oil is selected from castor oil, coconut oil, corn oil, ground nut oil, olive oil, palm oil, rapeseed oil, soybean oil, *arachis* oil, and sunflower oil.

17. A liquid formulation as claimed in claim 14, wherein the triglyceride-based oil comprises purified or fractionated triglycerides selected from medium chain triglycerides containing fatty acid residues of 6-12 carbon atoms in length and long chain triglycerides containing acid residues of more than 12 carbon atoms in length.

18. A liquid formulation as claimed in claim 17, wherein the triglyceride-based oil comprises predominantly medium-chain triglycerides.

19. A liquid formulation as claimed in claim 18, wherein the medium-chain triglycerides are capric/caprylic triglycerides.

20. A liquid formulation as claimed in claim 1, wherein the pharmaceutically acceptable oily carrier consists essentially of a triglyceride-based oil.

21. A liquid formulation as claimed in claim 20, wherein the pharmaceutically acceptable oily carrier also comprises a waxy compound, wherein a major proportion of said carrier comprises the triglyceride-based oil and a minor proportion of said carrier comprises the waxy compound.

22. A liquid formulation as claimed in claim 21, wherein the waxy compound is selected from a higher alkane; a lipid; a plant or animal wax; petrolatum wax; a long-chain aliphatic ester; a fatty acid that is solid at ambient temperature; an ester of dicarboxylic acid; and a polyethylene glycol that is solid at ambient temperature.

23. A liquid formulation for oral administration comprising an active pharmaceutical ingredient (API), a waxy compound, and a pharmaceutically acceptable oily carrier, characterised in that the API is a substance which may induce an adverse event upon a patient's stomach, and particles comprising said active pharmaceutical ingredient and said waxy compound are dispersed in said pharmaceutically acceptable oily carrier.

24. A method of treating a patient having or susceptible to a condition that may be ameliorated or prevented by an active pharmaceutical ingredient that is sensitive to the acidity of the patient's stomach, which method involves oral administration to the patient of a formulation according to claim 1.

25. A method of treating a patient having or susceptible to a condition that may be ameliorated or prevented by an active pharmaceutical ingredient that may induce an adverse event upon a patient's stomach, which method involves oral administration to the patient of a formulation according to claim 1.

* * * * *